United States Patent
Pevere et al.

(10) Patent No.: US 6,384,273 B1
(45) Date of Patent: May 7, 2002

(54) METHOD FOR ORTHOMETALATION OF A CARBOCYCLIC AROMATIC DERIVATIVE BEARING AT LEAST AN ELECTRON DONOR GROUP

(75) Inventors: Virginie Pevere, Lyons; Jean Roger Desmurs, St Symphorien d'Ozon; Charles Mioskowski; Alain Wagner, both of Strasbourg; Arnaud Gissot, Yerres, all of (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/700,467

(22) PCT Filed: May 14, 1999

(86) PCT No.: PCT/FR99/01163

§ 371 Date: Jan. 24, 2001

§ 102(e) Date: Jan. 24, 2001

(87) PCT Pub. No.: WO99/59941

PCT Pub. Date: Nov. 25, 1999

(30) Foreign Application Priority Data

May 15, 1998 (FR) .............................................. 98 06191

(51) Int. Cl.⁷ ................................................ C07C 65/00
(52) U.S. Cl. ....................... 562/473; 568/426; 568/442; 568/51; 568/33; 568/648
(58) Field of Search .......................... 562/473; 568/426, 568/442, 51, 33, 648

(56) References Cited

U.S. PATENT DOCUMENTS 4,845,277 A 7/1989 Yu

OTHER PUBLICATIONS

J.H. Adams; "Rutaceous Constituents—13. A Biomimetic Synthesis of Acroncycine", Tetrahedron, vol. 37, 1981, pp. 209–217, XP002091880.
G. Ehrhart; "Ueber Umsetzungen mit Phenylnatrium", Berichte Der Deutschen Chemischen Gesellschaft, vol. 96, No. 8, 1963, pp. 2042–2046, XP002091881.

Primary Examiner—Paul J. Killos
(74) Attorney, Agent, or Firm—Burns, Doane, Swecker & Mathis, L.L.P.

(57) ABSTRACT

The invention concerns a method for orthometalation of a carbocyclic aromatic derivative bearing at least an electron donor group, characterised in that it consists in reacting said carbocyclic aromatic derivative with an efficient amount of at least one alkaline metal in the presence of a compound of formula (I): RX, wherein: R represents a hydrocarbon radical having 1 to 20 carbon atoms which can be a saturated or unsaturated, linear or branched, acyclic aliphatic radical; a saturated or unsaturated, monocyclic or polycyclic cycloaliphatic radical; a saturated or unsaturated, linear or branched aliphatic radical bearing a cyclic substituent; and X represents a bromine or chlorine atom.

26 Claims, No Drawings

METHOD FOR ORTHOMETALATION OF A CARBOCYCLIC AROMATIC DERIVATIVE BEARING AT LEAST AN ELECTRON DONOR GROUP

The present invention relates to a process for the metallation of a carbocyclic aromatic derivative.

The invention is preferably directed towards the orthometallation of 1,3-dimethoxybenzene and more particularly to the preparation of 2,6-dimethoxybenzoic acid.

An o-metallation conventionally denotes a reaction leading to the generation of an anion in an ortho position relative to an electron-donating group present on an aromatic system.

More specifically, the present invention relates to an electrophilic addition to aromatic systems bearing an anion. This mechanism requires, in a first step, the loss of a leaving group, commonly a proton, prior to the addition of the electrophilic group which takes place in a consecutive step.

One of the approaches conventionally adopted for carrying out the first step consists in placing the aromatic derivative which it is desired to functionalize in contact with an organometallic compound in order to metallate it.

The usual reagent proposed for this reaction is butyllithium.

The major drawback of this metallation is precisely the use of butyllithium, which is an expensive reagent.

The reaction of sodium on 1,3-dimethoxybenzene in the presence of chlorobenzene, followed by a carboxylation has also been disclosed (G. Erhardt; Chem. Ber. 2042 (1963)). However, the reaction yield in terms of expected product remains very low on account of the formation of side products.

The object of the present invention is thus to propose a novel route for the metallation of aromatic derivatives which is more advantageous in terms of cost and yield than those mentioned above.

Consequently, a first subject of the present invention is a process for the ortho-metallation of a carbocyclic aromatic derivative bearing at least one electron-donating group, characterized in that the said carbocyclic aromatic derivative is reacted with an effective amount of at least one alkali metal in the presence of a compound of formula (I):

RX (I)

in which

R represents a hydrocarbon-based radical containing from 1 to 20 carbon atoms which may be a saturated or unsaturated, linear or branched acyclic aliphatic radical; a saturated, unsaturated, monocyclic or polycyclic cycloaliphatic radical; or a saturated or unsaturated, linear or branched aliphatic radical bearing a cyclic substituent; and X represents a bromine or chlorine atom.

In the account which follows of the present invention, the term "aromatic" means the conventional notion of aromaticity as defined in the literature, in particular by Jerry March, Advanced Organic Chemistry, 4th edition, John Wiley and Sons, 1992, pp. 40 et seq.

More specifically, a subject of the present invention is a process for the ortho-metallation of a carbocyclic aromatic derivative of general formula (II):

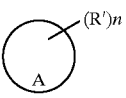
 (II)

in which:

A symbolizes the residue of a ring forming all or part of a monocyclic or polycyclic aromatic carbocyclic system, this system comprising at least one group R', the said cyclic residue possibly bearing one or more substituents, R' represents one or more substituents, which may be identical or different, of electron-donating nature, which are optionally linked together, and n is a non-zero integer less than or equal to 4.

The electron-donating nature of the radicals R' is assessed in the context of the present invention according to the scale of electronegativity established by Jerry March, "Advanced Organic Chemistry", 4th edition, John Wiley and Sons, 1992, pp. 14 et seq. The electronegative nature of a radical is evaluated with regard to that of the hydrogen atom, the value of which is 2.176.

As an illustration of the radicals which may be represented by R' in the general formula (II), mention may be made in particular of:

a linear or branched alkyl radical containing from 1 to 12 carbon atoms, the hydrocarbon-based chain possibly being interrupted with a hetero atom (for example oxygen), with a functional group (for example —CO—) and/or bearing a substituent such as, for example, an aromatic or non-aromatic cyclic substituent. It may be in particular a linear or branched alkyl radical containing from 1 to 6 carbon atoms, preferably from 1 to 4 carbon atoms, such as methyl, ethyl, propyl, isopropyl, butyl, isobutyl, sec-butyl or tert-butyl, or a linear or branched alkenyl radical containing from 2 to 6 carbon atoms, preferably from 2 to 4 carbon atoms, such as vinyl or allyl, or a $C_1$ to $C_{12}$ arylalkyl radical such as benzyl, a carbocyclic radical which is saturated or which comprises 1 or 2 unsaturations in the ring, generally containing from 3 to 8 carbon atoms and preferably 6 carbon atoms in the ring, the said ring possibly being substituted with substituents such as R'. It may be in particular a cycloalkyl group containing from 3 to 8 carbon atoms, such as a cyclohexyl group, and an aromatic carbocyclic radical, preferably a monocyclic radical, generally containing at least 4 carbon atoms and preferably 6 carbon atoms in the ring, the said ring possibly being substituted. It may in particular be phenyl;

$Z(R_1)$ with Z representing an oxygen or sulphur atom and $R_1$ corresponding to the definition proposed for R' above and preferably featuring a hydrogen atom, a linear or branched $C_1$ to $C_6$ and preferably $C_1$ to $C_4$ alkyl radical such as methyl, ethyl, propyl, ispropyl, butyl, isobutyl, sec-butyl or tert-butyl;

a $C_3$ to $C_8$ cycloalkyl radical such as cyclohexyl;

a fused or non-fused $C_5$ to $C_{12}$ aryl radical such as phenyl;

a $C_1$ to $C_{12}$ arylalkyl radical such as benzyl, and a trialkylsilyl radical,

—$R_2COOR_1$,

—R$_2$CO—N(R$_3$)$_2$,
—R$_2$—N(R$_3$)$_2$,
—R$_2$—CF$_3$;

with R$_2$ representing a valency bond or a linear or branched, saturated or unsaturated divalent hydrocarbon-based radical containing from 1 to 6 carbon atoms, such as, for example, methylene, ethylene, propylene, isopropylene or isopropylidene, and the radicals R$_3$, which may be identical or different, representing a hydrogen atom or a linear or branched alkyl radical containing from 1 to 6 carbon atoms, or alternatively two groups R' can be linked and form alkylenedioxy or alkylenedithio groups, preferably a methylenedioxy, ethylenedioxy, methylenedithio or ethylenedithio group.

It is understood that the list of examples of substituents R' given above has no limiting nature. Any substituent can be present on the ring provided that it remains inert under the reaction conditions, i.e. it does not interfere with the ortho-metallation reaction.

In the general formula (II) of the aromatic derivatives, the residue A can represent the residue of a monocyclic aromatic carbocyclic compound containing at least 4 carbon atoms and preferably 6 carbon atoms, or the residue of a polycyclic carbocyclic compound which can consist of at least 2 aromatic carbocycles and together forming ortho- or ortho- and peri-fused systems, or can consist of at least 2 carbocycles, at least one of which is aromatic, and together forming ortho- or ortho- and peri-fused systems. A naphthalene residue may be mentioned more particularly.

Residue A can bear one or more radicals R' on the aromatic ring.

The process of the invention applies most particularly to carbocylic aromatic derivatives substituted with at least one electron-donating radical featured by a group OR$_1$.

In the present text, the expression "alkoxy groups" denotes, in a simplified manner, groups of the type —O—R$_1$ in which R$_1$ has the meaning given above. R$_1$ thus represents either a saturated, unsaturated or aromatic, acyclic aliphatic or cycloaliphatic radical or a saturated or unsaturated aliphatic radical bearing an aromatic or non-aromatic, cyclic substituent, or alternatively a trialkylsilyl radical.

The carbocyclic aromatic ether which is involved in the process of the invention preferably corresponds to formula (II) in which R$_1$ in OR$_1$, represents a saturated or unsaturated, linear or branched acyclic aliphatic radical.

More preferably, R$_1$ of the aromatic ether represents a linear or branched alkyl radical containing from 1 to 12 carbon atoms and preferably from 1 to 6 carbon atoms, the hydrocarbon-based chain possibly being interrupted with a hetero atom (for example oxygen), with a functional group (for example —CO—) and/or bearing a substituent.

The saturated or unsaturated, linear or branched acyclic aliphatic radical can optionally bear a cyclic substituent. The term "ring" preferably means a saturated, unsaturated or aromatic carbocyclic ring, preferably a cycloaliphatic or aromatic ring, in particular a cycloaliphatic ring containing 6 carbon atoms in the ring, or a benzene ring.

The acyclic aliphatic radical can be linked to the ring by a valency bond, a hetero atom or a functional group as illustrated in the case of the definition of R'.

The ring can be optionally substituted and, as examples of cyclic substituents, substituents such as R' whose meaning is specified for formula (IIa) may be envisaged, inter alia.

R$_1$ can also represent a saturated carbocyclic radical or a carbocyclic radical comprising 1 or 2 unsaturations in the ring, generally containing from 3 to 8 carbon atoms and preferably 6 carbon atoms in the ring, the said ring possibly being substituted with substitutents such as those proposed for R'.

R$_1$ can also represent an aromatic carbocyclic radical, preferably a monocyclic radical generally containing at least 4 carbon atoms and preferably 6 carbon atoms in the ring, the said ring possibly being substituted with substituents such as those proposed for R'.

The process of the invention applies most particularly to the aromatic ethers of formula (II) in which R$_1$ represents a linear or branched alkyl radical containing from 1 to 4 carbon atoms, an arylalkyl radical or a trialkylsilyl radical.

As examples of radicals R$_1$ that are preferred according to the invention, mention may be made of methyl or ethyl, benzyl and trimethylsilyl radicals.

The process of the invention applies more particularly to the aromatic ethers of formula (IIa):

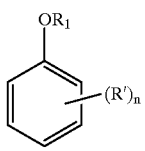

(IIa)

In formula (IIa), R$_1$ preferably represents a linear or branched alkyl radical containing from 1 to 4 carbon atoms, preferably a methyl or ethyl radical, or an arylalkyl radical or a trialkylsilyl radical, and R' and n are as defined above.

Aromatic ethers of formula (II) or (IIa) in which:

n ranges from 0 to 2,

R$_1$ represents a linear or branched alkyl radical containing from 1 to 4 carbon atoms, an arylalkyl radical and preferably a benzyl radical, or a trialkylsilyl radical, R$_1$ represents a linear or branched alkoxy radical containing from 1 to 4 carbon atoms, preferably a methoxy or ethoxy radical or a radical OR$_1$ with R$_1$ as defined above, are preferably involved in the process of the invention.

As illustrations of compounds corresponding to formula (II) or (IIa), mention may be made more particularly of:

monoethers such as anisole, ethoxybenzene (phenetole), propoxybenzene, isopropoxybenzene, butoxybenzene, isobutoxybenzene, benzyloxybenzene, 1-methoxynaphthalene, 2-methoxynaphthalene, 2-ethoxy-naphthalene; and substituted monoethers such as 1-methoxy-2-allyloxybenzene and phenoxytrimethylsilane;

diethers such as veratrole, 1,3-dimethoxy-benzene, 1,4-dimethoxybenzene, 1,2-diethoxybenzene, 1,3-diethoxybenzene, 1,2-dimethoxybenzene, 1,3-dipropoxybenzene, 1,2-methylenedioxybenzene, 1,2-ethylenedioxybenzene; 1,3-dibenzyloxybenzene; and 1,3-diphenolbise-trimethylsilyl;

triethers such as 1,3,5-trimethoxybenzene and 1,3,5-triethoxybenzene.

The compounds to which the process according to the invention applies in a more particularly advantageous manner are 1,3-dimethoxybenzene, anisole, 1,4-dimethoxybenzene, 1,2-dimethoxybenzene, 1,3-dibenzyloxybenzene and 1,3-diphenolbis-tert-butyldimethylsilyl.

As regards the compound of general formula (I), the compounds which are most particularly suitable for the invention are those in which R represents a linear or branched $C_1$ to $C_{10}$ alkyl group, $C_3$ to $C_{10}$ cycloalkyl group, $C_6$ to $C_{12}$ aryl group or $C_7$ to $C_{15}$ alkylaryl group, such as, for example, a benzyl radical.

More preferably, it is a $C_1$ to $C_{10}$ alkyl group and more preferably a $C_3$ to $C_{10}$ alkyl group in which the alkyl chain may possibly be interrupted with one or more oxygen atoms.

It is preferentially a chloroalkane and preferably chlorobutane or chlorooctane.

As regards the alkali metal used according to the invention, this may be sodium, lithium or potassium.

The process claimed is more particularly advantageous when sodium is used as alkali metal:

Specifically, it is quite probable that the reaction of the compound of general formula (I) with the alkali metal generates the carbanion $R^-$ which, by reaction with the carbocyclic aromatic derivative of general formula (II) or (IIa), leads to metallation of this derivative. However, in the case of the process claimed, the carbanion $R^-$ is advantageously generated in the presence of a carbocyclic aromatic derivative and thus reacts immediately with this derivative. Consequently, the process claimed makes it possible to significantly reduce the risks of spurious dimerization reactions, which are observed more particularly in the presence of sodium, and which consist of a reaction of the carbanion $R^-$ with a compound of general formula I.

This alkali metal can be introduced for the metallation reaction either in the form of a dispersion or in molten form.

The dispersed form, which is more advantageous in terms of reactivity, is generally preferred. This dispersed form, which is commercially available, can also be obtained in situ by vigorous stirring of the pre-fused metal.

The compound of general formula (I) is generally introduced in a proportion of at least one equivalent of the carbocylic aromatic derivative and preferably between about 1 and 2 equivalents. The alkali metal is present at between about 2 and 4 equivalents of the carbocyclic aromatic derivative and preferably between about 2 and 2.5 equivalents.

The reaction of the carbocyclic aromatic derivative with the compound of formula I and the alkali metal is carried out in an aprotic organic liquid which is inert under the appropriate reaction conditions.

As examples of solvents which are suitable for the present invention, mention may be made in particular of aliphatic or aromatic hydrocarbons, and aliphatic, cycloaliphatic or aromatic oxygen ethers.

As examples of aliphatic or cycloaliphatic hydrocarbons, mention may be made more particularly of paraffins such as, especially, hexane, heptane, octane, nonane, decane, undecane, dodecane, tetradecane or cyclohexane, and aromatic hydrocarbons such as, especially, benzene, toluene, xylenes, cumene, petroleum fractions consisting of a mixture of alkylbenzenes, in particular fractions of the Solvesso® type.

Aliphatic, cycloaliphatic or aromatic oxygen ethers, and more particularly diethyl ether, dipropyl ether, diisopropyl ether, dibutyl ether, methyl tert-butyl ether, dipentyl ether, diisopentyl ether, ethylene glycol dimethyl ether (or 1,2-dimethoxyethane), diethylene glycol dimethyl ether (or 1,5-dimethoxy-3-oxapentane); phenyl ether, benzyl ether; and dioxane, tetrahydrofuran (THF).

The preferred solvents are anhydrous aromatic hydrocarbons such as toluene, THF, xylenes and anhydrous analogues.

A mixture of organic solvents can also be used. Needless to say, the solvents selected should remain inert under the reaction conditions.

The concentration of the carbocyclic aromatic derivative in the medium can vary within a wide range. Thus, it may be between 5% and 40% by weight of the medium and is preferably about 20% by weight.

From a practical point of view, the ortho-metallation reaction is carried out by first loading the alkali metal into the organic solvent. The mixture is then kept stirring. Conversely, the consecutive addition of the carbocyclic aromatic derivative can be carried out according to two variants.

According to a first variant, the said derivative is introduced in the form of a mixture with the compound of general formula (I). This mixture is preferably added to the reaction medium gradually.

The other variant preferably selected consists in successively adding the carbocyclic aromatic derivative and then the compound of general formula (I).

Generally, the various compounds are introduced at a temperature of between −20° C. and 50° C. and preferably at room temperature. Subsequent heating of the reaction medium to a temperature of between 20° C. and 100° C. and more preferably between 40° C. and 60° C. may possibly be advantageous.

The reaction is generally carried out at atmospheric pressure. The reaction is preferably carried out under a controlled atmosphere of inert gases such as nitrogen or rare gases such as argon.

The progress of the metallation reaction may be monitored, where appropriate, by visualizing the disappearance of the alkali metal. At the end of the reaction, the metallated form of the carbocyclic aromatic derivative is present in the reaction medium in a dissolved form. Where appropriate, the excess alkali metal is neutralized.

The product of the ortho-metallation reaction is not isolated but rather is used in the form as generated to produce derivatives of the compound of general formula (II) or (IIa).

An organic compound capable of interacting with the said metallation product by electrophilic substitution is generally introduced into the reaction medium.

As non-limiting illustrations of organic compounds of this type, mention may be made in particular of the following compounds:
—$SO_2$,
—$CO_2$,
—$CS_2$,
—$(R_5)_2NCHO$,
—$(CH_2O)_{n'}$, with n' being an integer ranging from 1 to 3,
—paraformaldehyde,
—$(R_5O)_2SO_2$,
—$R_5SiX'$,
—$ArCH_2X'$,
—$R_5$—S—S—$R_5$,
—$R_5SO_2$—O—$O_2SR_5$,
—$R_5X'$,
—$B(OR_5)_3$,
—$R_5SO_2X'$,
—$ArCOX'$,
with $R_5$ representing a linear or branched $C_1$ to $C_{12}$ alkyl radical or a $C_3$ to $C_{12}$ cycloalkyl radical, or a trifluoromethyl radical, and X' representing a halogen atom such as chlorine or bromine.

The reaction itself can be carried out in a conventional manner.

The electrophilic derivative is conventionally introduced in a proportion of about from 1.0 to 2 equivalents, relative to the metallated carbocyclic aromatic derivative, and preferably about 1 to 1.5.

The reaction can be carried out at a temperature of between 20° C. and 80° C. and preferably between 20° C. and 50° C. It is generally carried out at atmospheric pressure and under an inert atmosphere.

The reaction product can be isolated after the substitution reaction by any conventional technique of extraction type, for example.

One specific embodiment of the invention relates in particular to the preparation of 2,6-dimethoxybenzoic acid from 1,3-dimethoxybenzene.

More specifically, a subject of the present invention is a process for preparing 2,6-dimethoxybenzoic acid from 1,3-dimethoxybenzene via the ortho-metallation of the latter, characterized in that the said metallation is carried out by reacting 1,3-dimethoxybenzene with an alkali metal in the presence of a compound of general formula (I):

RX     (I)

in which

R represents a hydrocarbon-based radical containing from 1 to 20 carbon atoms which may be a saturated or unsaturated, linear or branched acyclic aliphatic radical; a saturated, unsaturated, monocyclic or polycyclic cycloaliphatic radical; or a saturated or unsaturated, linear or branched aliphatic radical bearing a cyclic substituent; and X represents a bromine or chlorine atom.

The alkali metal is as defined previously. It is preferably sodium.

According to one embodiment of the invention, it is combined with chlorooctane.

As regards the stoichiometry and the operating parameters which are suitable for carrying out the said metallation reaction, reference will be made to the information given previously.

The examples given below are presented as non-limiting illustrations of the present invention.

EXAMPLE 1

Preparation of 2,6-Dimethoxybenzoic Acid 5.90 g (0.256 M) of sodium and 200 ml of anhydrous toluene are introduced into a reactor. The mixture is refluxed for 30 min and then stirred vigorously at room temperature.

12.6 g (0.09 M) of 1,3-dimethoxybenzene and 17.7 g (0.119 M) of chlorooctane are then added successively. After stirring for 2 h at room temperature, about 35 g of $CO_2$ are added and the reaction is stirred for 12 h at room temperature.

The excess sodium is then neutralized with 10 ml of methanol.

After acidification using concentrated hydrochloric acid solution, the medium is concentrated under partial pressure.

The residue is dissolved in acetone. The inorganic salts are removed by filtration. Recrystallization is carried out in an acetone/hexane mixture. 11.3 g of 2,6-dimethoxybenzoic acid (yield=68%) are thus obtained.

Characteristics of the product obtained:

$^1H$ NMR $(DMSO-d^6)$ = 3.89 ppm $(s, 6H)$ 6.60 ppm $(d, 2H)$ 7.34 ppm $(t, 1H)$ 8–9 ppm $(s, 1H)$ By replacing the chlorooctane with chloropropane, 2,6-dimethoxybenzoic acid is obtained in a yield of 71%.

EXAMPLES 2–8

Preparation of 2,6-Dimethoxy Substituted Aryl Compounds

The ortho-metallation of 1,3-dimethoxybenzene is carried out under the same conditions as in Example 1, in the presence of chlorooctane. The nature of the electrophile used is then different:

| Example | Electrophile | Product formed | Isolated yield |
|---|---|---|---|
| Example 2 | $(CH_3)_2NCHO$ | 2,6-dimethoxybenzaldehyde (CHO with $H_3CO$, $OCH_3$) | 43% |
| Example 3 | $PhCH_2Br$ (*) | $CH_2Ph$ with $H_3CO$, $OCH_3$ | 75% |
| Example 4 | $(CH_3)_2SO_4$ (*) | $CH_3$ with $H_3CO$, $OCH_3$ | 70% |
| Example 5 | $CH_3SO_2Cl$ (*) | $SO_2CH_3$ with $H_3CO$, $OCH_3$ | 20% |
| Example 6 | $(CH_3)_3SiCl$ (*) | $Si(CH_3)_3$ with $H_3CO$, $OCH_3$ | 75% |
| Example 7 | $B(OCH_3)_2$ (*) | $B(OCH_3)_2$ with $H_3CO$, $OCH_3$ | 20% |

-continued

| Example | Electrophile | Product formed | Isolated yield |
|---|---|---|---|
| Example 8 | (CH₃)S—S(CH₃) (*) | 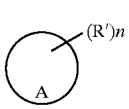 | 50% (NMR) |

(*): use of a commercial Na/toluene suspension

EXAMPLE 9

Comparative Test

Example 4 is reproduced, replacing the chlorooctane with chlorobenzene.

The isolated yield of 2,6-dimethoxytoluene is 5 34%, with formation of 36% of a side product, 2,6-dimethoxybiphenyl.

EXAMPLES 10–12

Preparation of Benzoic Acid Derivatives

The ortho-metallation reaction is carried out as in Example 1, using different substrates and $CO_2$ as electrophile.

| Example | Substrate | Product formed | Isolated yield |
|---|---|---|---|
| Example 10 (*) | OCH₃ (phenyl) | OCH₃, COOH (ortho) | 35% |
| Example 11 (*) | 1,4-dimethoxybenzene | 2,5-dimethoxybenzoic acid | 88% |
| Example 12 (*) | 1,2-dimethoxybenzene | 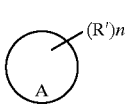 | 80% |

(*): use of a commercial Na/toluene suspension

What is claimed is:

1. A process for the ortho-metallation of a carbocyclic aromatic derivative bearing at least one electron-donating group, comprising reacting said carbocyclic aromatic derivative with an effective amount of at least one alkali metal in the presence of a compound of formula (I):

$$RX \qquad (I)$$

in which:

R represents a hydrocarbon-based radical comprising from 1 to 20 carbon atoms which may be a saturated or unsaturated, linear or branched acyclic aliphatic radical; a saturated, unsaturated, monocyclic or polycyclic cycloaliphatic radical; or a saturated or unsaturated, linear or branched aliphatic radical bearing a cyclic substituent; and represents a bromine or chlorine atom.

2. The process according to claim 1, wherein the carbocyclic aromatic derivative corresponds to the general formula (II):

$$(II)$$

in which:

A symbolizes the residue of a ring forming all or part of a monocyclic or polycyclic aromatic carbocyclic system, this system comprising at least one group R', said cyclic residue optionally bearing one or more substituents, R' represents one or more substituents, which may be identical or different, of electron-donating nature, which are optionally linked together, and n is a non-zero integer less than or equal to 4.

3. The process according to claim 1, wherein the carbocyclic aromatic derivative corresponds to the general formula (II):

$$(II)$$

in which:

A symbolizes the residue of a ring forming all or part of a monocyclic or polycyclic aromatic carbocyclic system, this system comprising at least one group R', said cyclic residue optionally bearing one or more substituents, R' is at least one radical selected from the group consisting of:
a linear or branched alkyl radical containing from 1 to 12 carbon atoms, the hydrocarbon-based chain optionally being interrupted with a hetero atom, with a functional group and/or bearing a substituent,
a carbocyclic radical which is saturated or which comprises 1 or 2 unsaturations in the ring, comprising from 3 to 8 carbon atoms in the ring, said ring optionally being substituted with substituents comprising R', and
an aromatic carbocyclic radical comprising at least 4 carbon atoms in the ring, said ring optionally being substituted, $Z(R_1)$ with Z representing an oxygen or sulphur atom and $R_1$ corresponding to the definition proposed for R' above and optionally featuring
a hydrogen atom,
a linear or branched $C_1$ to $C_6$ alkyl radical;
a $C_3$ to $C_8$ cycloalkyl radical;
a fused or non-fused $C_5$ to $C_{12}$ aryl radical;
a $C_1$ to $C_{12}$ arylalkyl radical; or a trialkylsilyl radical,
—R$_2$COOR1,
—R$_2$CO—N(R$_3$)$_2$,
—R$_2$—N(R$_3$)$_2$,
—R$_2$—CF$_3$;
with R$_2$ representing a valency bond or a linear or branched, saturated or unsaturated divalent hydrocarbon-based radical containing from 1 to 6 carbon atoms, and the radicals R$_3$, which may be identical or different, representing a hydrogen atom or a linear or branched alkyl radical containing from 1 to 6 carbon atoms, or alternatively two groups R' can be linked and form alkylenedioxy or alkylenedithio groups.

4. The process according to claim 1, wherein carbocyclic aromatic derivative corresponds to the general formula (II):

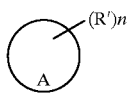

(II)

in which:

the residue A represents the residue of a monocyclic aromatic carbocyclic compound containing at least 4 carbon atoms, or the residue of a polycyclic carbocyclic compound which can comprise at least 2 aromatic carbocycles and together forming ortho- or ortho- and peri-fused systems, or comprise at least 2 carbocycles, at least one of which is aromatic, and together forming ortho- or ortho- and peri-fused systems, R' is at least one radical selected from the group consisting of:
  a linear or branched alkyl radical comprising from 1 to 12 carbon atoms, the hydrocarbon-based chain optionally being interrupted with a hetero atom, with a functional group and/or bearing a substituent;
  a carbocyclic radical which is saturated or which comprises 1 or 2 unsaturations in the ring, comprising from 3 to 8 carbon atoms in the ring, said ring optionally being substituted with substituents comprising R', and
  an aromatic carbocyclic radical, containing at least 4 carbon atoms in the ring, said ring optionally being substituted;

Z(R$_1$) with Z representing an oxygen or sulphur atom and R$_1$ corresponding to the definition proposed for R' above and optionally featuring
  a hydrogen atom,
  a linear or branched C$_1$ to C$_6$ alkyl radical;
  a C$_3$ to C$_8$ cycloalkyl radical;
  a fused or non-fused C$_5$ to C$_{12}$ aryl radical;
  a C$_1$ to C$_{12}$ arylalkyl radical; and
  a trialkylsilyl radical,
R$_2$COOR$_1$,
—R$_2$CO—N(R$_3$)$_2$,
—R$_2$—N(R$_3$)$_2$,
—R$_2$—CF$_3$;
  with R$_2$ representing a valency bond or a linear or branched, saturated or unsaturated divalent hydrocarbon-based radical comprising from 1 to 6 carbon atoms, and the radicals R$_3$, which may be identical or different, representing a hydrogen atom or a linear or branched alkyl radical comprising from 1 to 6 carbon atoms, or alternatively two groups R' can be linked and form alkylenedioxy or alkylenedithio groups, n is a non-zero integer less than or equal to 4.

5. The process according to claim 1, wherein the carbocyclic aromatic derivative corresponds to the general formula (II):

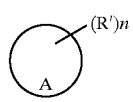

(II)

in which:

the residue A represents the residue of a monocyclic aromatic carbocyclic compound containing at least 4 carbon atoms, or the residue of a polycyclic carbocyclic compound which can comprise at least 2 aromatic carbocycles and together forming ortho- or ortho- and peri-fused systems, or comprise at least 2 carbocycles, at least one of which is aromatic, and together forming ortho- or ortho- and peri-fused systems, and the electron-donating substituent represented by R' is at least one group OR$_1$ with R$_1$ featuring:
  a hydrogen atom,
  a linear or branched C$_1$ to C$_6$ alkyl radical;
  a C$_3$ to C$_8$ cycloalkyl radical;
  a fused or non-fused C$_5$ to C$_{12}$ aryl radical;
  a C$_1$ to C$_{12}$ arylalkyl radical;
  a trialkylsilyl radical.

6. The process according to claim 1, wherein the carbocyclic aromatic derivative corresponds to the general formula (II):

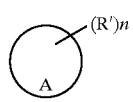

(II)

in which:

the residue A represents the residue of a monocyclic aromatic carbocyclic compound containing at least 4 carbon atoms, or the residue of a polycyclic carbocyclic compound which can comprise at least 2 aromatic carbocycles and together forming ortho- or ortho- and peri-fused systems, or comprise at least 2 carbocycles, at least one of which is aromatic, and together forming ortho- or ortho- and peri-fused systems, and the electron-donating substituent represented by R' is at least one group OR$_1$ with R$_1$ representing a linear or branched alkyl radical containing from 1 to 4 carbon atoms, an arylalkyl radical or a trialkylsilyl radical.

7. The process according to claim 1, wherein the carbocyclic aromatic derivative corresponds to the general formula (IIa):

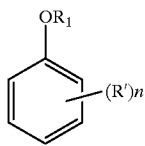
(IIa)

in which:
R$_1$ represents a linear or branched alkyl radical containing from 1 to 4 carbon atoms or an arylalkyl radical or a trialkylsilyl radical,
R' is at least one radical selected from the group consisting of:
  a linear or branched alkyl radical containing from 1 to 12 carbon atoms, the hydrocarbon-based chain optionally being interrupted with a hetero atom, with a functional group and/or bearing a substituent,
  a carbocyclic radical which is saturated or which comprises 1 or 2 unsaturations in the ring, comprising from 3 to 8 carbon atoms in the ring, said ring possibly being substituted with substituents such as R', and
  an aromatic carbocyclic radical, comprising at least 4 carbon atoms in the ring, said ring optionally being substituted;
Z(R$_1$) with Z representing an oxygen or sulphur atom and R$_1$ corresponding to the definition proposed for R' above and optionally featuring a hydrogen atom,
  a linear or branched C$_1$ to C$_6$ alkyl radical;
  a C$_3$ to C$_8$ cycloalkyl radical;
  a fused or non-fused C$_5$ to C$_{12}$ aryl radical;
  a C$_1$ to C$_{12}$ arylalkyl radical; or
  a trialkylsilyl radical,
—R$_2$COOR$_1$,
—R$_2$CO—N(R$_3$)$_2$,
—R$_2$—N(R$_3$)$_2$,
—R$_2$—CF$_3$;
  with R$_2$ representing a valency bond or a linear or branched, saturated or unsaturated divalent hydrocarbon-based radical containing from 1 to 6 carbon atoms, and the radicals R$_3$, which may be identical or different, representing a hydrogen atom or a linear or branched alkyl radical containing from 1 to 6 carbon atoms, or alternatively
two groups R' can be linked and form alkylenedioxy or alkylenedithio groups, and
n is a non-zero integer less than or equal to 4.

8. The process according to claim 1, wherein the carbocyclic aromatic derivative corresponds to the general formula (IIa):

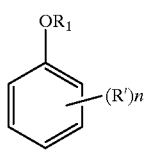
(IIa)

in which:
n ranges from 0 to 2,
R$_1$ represents a linear or branched alkyl radical containing from 1 to 4 carbon atoms, an arylalkyl radical or a trialkylsilyl radical,
R' represents a linear or branched alkoxy radical containing from 1 to 4 carbon atoms, or a radical OR$_1$ with R$_1$ as defined above.

9. The process according to claim 1, wherein the carbocyclic aromatic derivative is selected from the group consisting of:
  monoethers comprising anisole, ethoxybenzene (phenetole), propoxybenzene, isopropoxybenzene, butoxybenzene, isobutoxybenzene, 1-methoxynaphthalene, 2-methoxynaphthalene, 2-ethoxynaphthalene; and substituted monoethers such as 1-methoxy-2-allyloxybenzene, benzyloxybenzene, or phenoxytrimethylsilane; diethers comprising veratrole, 1,3-dimethoxybenzene, 1,4-dimethoxybenzene, 1,2-diethoxybenzene, 1,3-diethoxybenzene, 1,2-dimethoxybenzene, 1,3-dipropoxybenzene, 1,2-methylenedioxybenzene, 1,2-ethylenedioxybenzene; 1,3-dibenzyloxybenzene; or 1,3-diphenolbis-trimethylsilyl; and
  triethers comprising 1,3,5-trimethoxybenzene and 1,3,5-triethoxybenzene.

10. The process according to claim 1, wherein in the compound of general formula (I), R represents a group selected from the group consisting of linear or branched C$_1$ to C$_{10}$ alkyl, C$_3$ to C$_{10}$ cycloalkyl, C$_6$ to C$_{12}$ aryl or C$_7$ to C$_{15}$ alkylaryl.

11. The process according to claim 1, wherein the compound of general formula (I) is a chloroalkane.

12. The process according to claim 1, wherein the alkali metal is selected from the group consisting of lithium, sodium and potassium.

13. The process according to claim 1, wherein the alkali metal is sodium in a dispersed form.

14. The process according to claim 1, wherein the compound of general formula (I) is introduced in a proportion of at least one equivalent of the carbocyclic aromatic derivative.

15. The process according to claim 1, wherein the alkali metal is present at between about 2 and 4 equivalents of the carbocyclic aromatic derivative.

16. The process according to claim 1, wherein the reaction of the carbocyclic aromatic ether with the compound of formula (I) and the alkali metal is carried out in an aprotic organic liquid which is inert under the appropriate reaction conditions.

17. The process according to claim 1, wherein the reaction of the carbocyclic aromatic ether with the compound of formula (I) and the alkali metal is carried out in a solvent selected from the group consisting of toluene, THF, xylenes and anhydrous analogues.

18. The process according to claim 1, wherein the concentration of the aromatic derivative is between 5% and 40% by weight of the medium.

19. The process according to claim 1, wherein the ortho-metallation reaction is carried out by first loading the alkali metal into the organic solvent.

20. The process according to claim 1, wherein the ortho-metallation reaction is carried out by first loading the alkali metal into the organic solvent and the aromatic carbocyclic derivative is then introduced by mixing with the compound of general formula (I).

21. The process according to claim 1, wherein the ortho-metallation reaction is carried out by first loading the alkali metal into the organic solvent and the carbocyclic aromatic derivative and the compound of general formula (I) are then successively added.

22. The process according to claim 1, wherein the product of the metallation reaction is not isolated but rather is placed in contact in situ with an organic compound capable of reacting with it by electrophilic substitution.

23. A process for preparing 2,6-dimethoxybenzoic acid from 1,3-dimethoxybenzene via the ortho-metallation of the latter, wherein said metallation is carried out by reacting 1,3-dimethoxybenzene with an alkali metal in the presence of a compound of general formula (I):

$$RX \qquad (I)$$

in which

R represents a hydrocarbon-based radical containing from 1 to 20 carbon atoms which may be a saturated or unsaturated, linear or branched acyclic aliphatic radical; a saturated, unsaturated, monocyclic or polycyclic cycloaliphatic radical; or a saturated or unsaturated, linear or branched aliphatic radical bearing a cyclic substituent; and X represents a bromine or chlorine atom.

24. The process according to claim 23, wherein the compound of general formula (I) is chlorcoctane.

25. The process according to claim 23, wherein the alkali metal is sodium.

26. The process according to claim 23, wherein the compound of general formula (I) is chlorooctane and the alkali metal is sodium.

* * * * *